United States Patent
Chou et al.

(10) Patent No.: US 9,775,824 B2
(45) Date of Patent: Oct. 3, 2017

(54) MAGNETIC NANOPARTICLE COMPOSITION AND MANUFACTURING METHOD AND USE THEREOF

(71) Applicant: National Taiwan University, Taipei (TW)

(72) Inventors: Pi-Tai Chou, Taipei (TW); Chien-Liang Liu, New Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 317 days.

(21) Appl. No.: 14/295,442

(22) Filed: Jun. 4, 2014

(65) Prior Publication Data

US 2015/0352231 A1 Dec. 10, 2015

(51) Int. Cl.
*A61K 9/16* (2006.01)
*A61K 31/295* (2006.01)
*A61K 49/18* (2006.01)

(52) U.S. Cl.
CPC ........ *A61K 31/295* (2013.01); *A61K 49/1866* (2013.01); *Y10T 428/2982* (2015.01)

(58) Field of Classification Search
CPC .................................. A61B 5/00; A61K 49/00
See application file for complete search history.

(56) References Cited

U.S. PATENT DOCUMENTS

| | | | | |
|---|---|---|---|---|
| 2005/0271745 A1* | 12/2005 | Gruettner | ............... | A61K 33/26 424/646 |
| 2008/0213189 A1* | 9/2008 | Lee | .................. | A61K 47/48215 424/9.32 |
| 2008/0241262 A1* | 10/2008 | Lee | ...................... | A61K 9/0009 424/490 |
| 2011/0105825 A1* | 5/2011 | Nayfach-Battilana | ............ | A61K 41/0052 600/12 |
| 2014/0024026 A1* | 1/2014 | Alocilja | ............. | G01N 33/5434 435/6.11 |

OTHER PUBLICATIONS

Iron Oxide fact sheet (https://en.wikipedia.org/wiki/Iron(II)_oxide).*
Iron (II) oxide fact sheet (https://en.wikipedia.org/wiki/Iron(II)_oxide).*

* cited by examiner

*Primary Examiner* — Micah Paul Young
(74) *Attorney, Agent, or Firm* — Hsiu-Ming Saunders; Intellectual Property Connections, Inc.

(57) ABSTRACT

The present invention provides a magnetic nanoparticle composition, comprising an iron oxide particle core conjugated with a capping agent and having wüstite structure and antiferromagnetic properties, wherein the empirical formula of iron oxide is defined as $Fe_xO$ with x in the range of about 0.83 to about 0.96. Also provided are a method of manufacturing the same, a contrast agent comprising the same, and methods of using the same for acquiring a magnetic resonance image and for delivering a therapeutic or diagnostic agent.

19 Claims, 1 Drawing Sheet

MAGNETIC NANOPARTICLE COMPOSITION AND MANUFACTURING METHOD AND USE THEREOF

FIELD OF THE INVENTION

The present invention relates to magnetic nanoparticle compositions, such as contrast agents, useful in magnetic resonance imaging for disease diagnosis and/or treatment. In particular, this invention relates to iron oxide nanoparticles with wüstite structure and antiferromagnetic properties and having low magnetization and good water-dispersibility.

BACKGROUND OF THE INVENTION

Magnetic resonance imaging (MRI) is well known for its high resolution, unlimited tissue penetration in depth and absence of ionizing radiation that exceeds other biomedical imaging modality. Generally, contrast agents (CAs) for MRI are classified into T2-weighted ($r_2/r_1$ ratio$\gg$1) and T1-weighted ($r_2/r_1$ ratio close to 1) types.

For T2 CAs, superparamagnetic iron oxide nanoparticles (NPs) with high r2 relaxivities have been used in clinical hepatic tumor detection. However, T2-weighted imaging that produces negative contrast usually raises confusion with the signals from hemorrhage because both of which exhibit negative signals.

On the other hand, the T1-weighted counterpart, dubbed as the positive contrast, is subject to less artefacts and has higher signal intensity of the vascularized tissues, thereby providing advantageous alternatives. However, many clinically available T1 CAs, such as Gd-based (e.g. Gd-complexes, $Gd_2O_3$ NPs) and Mn-based (e.g. MnO, $Mn_3O_4$ NPs) CAs, are potentially hazardous or even life-threatening.

Accordingly, it is urgent to develop new contrast agents with both superior contrast and high biocompatibility.

SUMMARY OF THE INVENTION

In one aspect, the present invention is directed to a magnetic nanoparticle composition, which comprises an iron oxide particle core conjugated with a capping agent. The iron oxide particle core demonstrates antiferromagnetic properties and has an empirical formula defined as $Fe_xO$, with x in the range of about 0.83 to about 0.96, which is also known as the wüstite structure.

Theoretically, wüstite refers to a group of iron oxides which have a rock-salt structure with Fe and O forming nonstoichiometric $Fe_xO$ (x=0.83 to 0.96 approximately) and Fe vacancies in an ordered distribution. The structure is not chemically stable and is prone to decomposition into $\alpha$-Fe and inverse spinel $Fe_3O_4$ through a two-step disproportionation process or to oxidation to form $Fe_3O_4$, $\gamma$-$Fe_2O_3$, and/or $\alpha$-$Fe_2O_3$. This chemical reactivity makes $Fe_xO$ nanoparticles difficult to make, and those prepared from the high-temperature solution-phase decomposition of iron salt have not been fully characterized.

In one or more embodiments, the iron oxide particle core with wüstite structure exhibits an $r_2/r_1$ ratio of about 1 to about 10, such as about 2 to about 3, which makes the composition an ideal candidate as a T7 contrast agent.

In one or more embodiments, the composition is preferably prepared in an aqueous phase and is capable of retaining the $T_1$-weighted MR properties for a long period of time, such as more than 6 months. In addition, the composition may be preserved in a wide range of pH values, from about 4 to about 12, such as 5-10 or 6-8, and preferably preserved in a neutral condition. In some embodiments, the pH value may be changed to adjust the relaxivity to a desirable extent.

In one or more embodiments, the particle size of iron oxide particle core, which may be presented as an average of measurements from a plurality of particles, such as 100 particles, is less than 200 nm, less than 100 nm, less than 50 nm, less than 30 nm, less than 20 nm, less than 10 nm, less than 5 nm, or less than 3 nm. Generally, a smaller iron oxide particle core is preferred such that a solution or composition containing these nanoparticles has a greater water contact area and therefore stronger T1 signal. However, due to the antiferromagnetic properties of the iron oxide particle cores of this invention, particle size is not a determinative factor for the applicability of the composition as a contrast agent, but those containing smaller iron oxide particle cores are preferable.

In one or more embodiments, the capping agent is preferably a biocompatible capping agent so as to increase biocompatibility and reduce health concerns when the composition is administered to a subject or recipient such as an animal, particularly human. Preferably, the biocompatible capping agent is selected from a group consisting of glutathione, glutamic acid, dextrin, starch, glucose, chitosan, citrate, citric acid, ascorbic acid, insulin, bovine serum albumin, keratin, arginine, curcumin and protamine, and more preferably the biocompatible capping agent is glutathione, which is an antioxidant abundant in human body, thereby ensuring excellent biocompatibility of the composition.

In one or more embodiments, the capping agent and/or the iron oxide particle core is optionally conjugated with an agent for labeling, detecting, targeting or treating, such as a targeting agent or a therapeutic agent. The targeting agent is preferably a biotargeting agent selected from a group consisting of tissue-specific fluorophore, chromophore, protein, peptide, antibody, antibody fragment, antigen and hapten. The therapeutic agent is preferably selected from a group consisting of pharmaceutically active substance (such as drug), immunomodulator, cytokine, hormone, hormone antagonist, growth factor, enzyme, enzyme inhibitor, cytotoxic substance, and angiogenesis inhibitor.

The present invention is also directed to a method of manufacturing a magnetic nanoparticle composition. In one embodiment, the method comprises preparing a mixture containing ferrous salt, ferric salt and a capping agent; and adding a reducing agent to the mixture to initiate a redox reaction at room temperature, thereby forming a composition comprising iron oxide particle cores in an aqueous phase.

According to this invention, a facile one-step synthesis of the nanoparticle composition in aqueous phase and at room temperature can be established, greatly simplifying the synthesis process when compared to conventional multi-step processes for nanoparticle syntheses which are time-consuming, complicated, and less efficient. Moreover, the whole synthesis process does not involve the use of organic solvents, surfactants or toxic chemicals, and therefore requires no desolvation or separation after the completion of the reaction. In one embodiment, then the redox reaction is about to complete, the pH value of the composition spontaneously decreases to about 7 due to the hydroxide ion consumption, and the resulting iron oxide particles may be purified by centrifuged filtration. Therefore, the composition is useful for medical, therapeutic or diagnostic purposes and requires no or minimal additional neutralization step.

In one or more embodiments, the molar ratio of [$Fe^{2+}$] to [$Fe^{3+}$] is about 0.1 to about 10, such as about 0.2 to about 5, preferably about 0.5 to about 2, such as about 1. The reducing agent is preferably selected from a group consisting of tetrakis(hydroxymethyl)phosphonium chloride, borohydride, hydrazine, caustic alkali, hydroxyl amine, ammonium hydroxide, citrate, citric acid, and ascorbic acid; preferably, the reducing agent is tetrakis(hydroxymethyl) phosphonium chloride. As the starting material, the ferrous salt may be selected from various sources, such as from a group consisting of ferrous chloride, ferrous chloride tetrahydrate, ferrous acetate, ferrous lactate and ferrous oxalate, used alone or as a combination of two or more; similarly, the ferric salt may be selected from a group consisting of ferric chloride, ferric chloride hexahydrate, ferric acetate, ferric acetylacetonate, ferric oxalate, ferric nitrate and ferric nitrate nonahydrate, used alone or as a combination of two or more.

In one or more embodiments, the capping agent is preferably a biocompatible capping agent selected from a group consisting of glutathione, glutamic acid, dextrin, starch, glucose, chitosan, citrate, citric acid, ascorbic acid, insulin, bovine serum albumin, keratin, arginine, curcumin and protamine, and more preferably the biocompatible capping agent is glutathione.

The present invention is further directed to a contrast agent, preferably a biocompatible contrast agent having no or minimal toxicity. The contrast agent is a magnetic nanoparticle composition comprising iron oxide particle cores conjugated with capping agents, wherein the iron oxide particle cores exhibits wüstite structure and antiferromagnetic properties. In one preferred embodiment, the contrast agent is a $T_1$ contrast agent.

The present invention is further directed to a method of acquiring an image, comprising first administering a biocompatible contrast agent comprising the iron oxide particle cores mentioned above to a recipient or a subject; and acquiring a magnetic resonance image therefrom. Preferably, the contrast agent is a $T_1$ contrast agent and is co-administered with a pharmaceutically acceptable carrier, such as sterile saline or physiologically acceptable buffer.

The present invention is further directed to a method for delivering a therapeutic or diagnostic agent, wherein the therapeutic or diagnostic agent is co-administered with the aforesaid contrast agent to a recipient or subject.

Other and further aspects, features and advantages of the present invention will be apparent from the following description of the presently preferred embodiments of the invention given for the purpose of disclosure.

BRIEF DESCRIPTION OF THE DRAWINGS

For a better understanding of the present invention, reference is made to a detailed description to be read in conjunction with the accompanying drawings, in which.

DETAILED DESCRIPTION OF THE PREFERRED EMBODIMENTS

Figure 1:
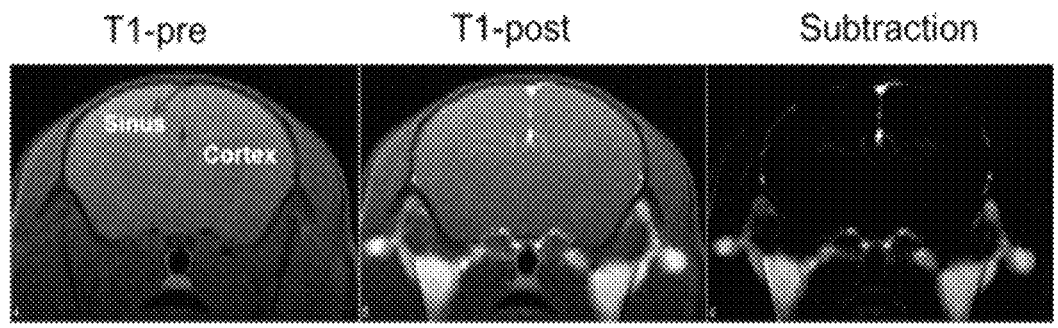
FIG. 1 shows in vim mice brain $T_1$ weighted image.

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

In order to explain the concepts and principles behind this invention, various embodiments are described herein. However, there is no intention to be bound by any expressed or implied theory presented in the preceding technical field, background, brief summary or the following detailed description.

In addition, unless otherwise defined, all technical and scientific terms used herein have the same meaning as commonly understood by one of ordinary skill in the art to which this invention pertains. In the case of conflict, the present document including definitions controls.

As used herein, the singular forms "a." "an," and "the" do not preclude plural referents, unless the content clearly dictates otherwise. As an example, for a composition comprising an iron oxide particle core, a plurality of iron oxide particle cores may present in the composition.

As used herein, the terms "comprises," "comprising," "includes," "including." "has." "having" or any other variation thereof are intended to cover a non-exclusive inclusion. For example, a composition that comprises a list of elements is not necessarily limited to only those elements but may include other elements not expressly listed or inherent to such composition. In addition, a composition comprises one form of iron oxide, such as $Fe_xO$, does not exclude the possible presence of other forms of iron oxide, such as $Fe_2O_3$, which is generally at a smaller amount relative to the major component $Fe_xO$.

Further, unless expressly stated to the contrary, the term "or" refers to an inclusive or and not to an exclusive or. For example, a condition "A or B" is satisfied by any one of the following: A is true (or present) and B is false (or not present), A is false (or not present) and B is true (or present), and both A and B are true (or present).

As used herein, "around" or "about" shall generally mean within 20 percent, preferably within 10 percent, and more preferably within 5 percent of a given value or range. Generally, numerical quantities given herein are approximate, meaning that the term "around" or "about" can be inferred if not expressly stated.

The term "treating" or "treatment" refers to administration of an effective amount of a substance to a subject with the purpose to cure, alleviate, relieve, remedy, ameliorate, or prevent a medical condition, the symptoms of it, or the predispositions towards it. As used herein, "effective amount" refers to an amount that may be therapeutically effective to inhibit, prevent, or treat a symptom of a particular disease, disorder, condition, or side effect described herein. For example, "an effective amount" may refer to the amount that is required to confer a therapeutic or a desired effect on the treated subject or recipient. Effective amount will vary, as recognized by those skilled in the art, depending on route of administration and the possibility of co-usage with other substances.

The term "recipient" or "subject" includes humans, and the terms "human," "patient," "recipient," and "subject" are used interchangeably herein.

As used herein, the term "nanoparticle" refers to a particle having a largest dimension of less than 500 nanometers, preferably less than 200 nm, and more preferably less than 100 nm. For example, a nanoparticle may have a particle size of about 150 nm, 50 nm, 40 nm, 30 nm, 20 nm, 10 nm, or less.

As used herein, the term "capping agent" refers to any molecule that is capable of forming linkage to, via a coordination bond for example, a transition metal ion, particularly iron, thus acting as a ligand for the transition metal. Preferably, the capping agent has an additional functional group available for reaction with a complementary functional group of another molecule, such as a targeting agent, a therapeutic agent or an analyte molecule that is to be labelled. The term "conjugation" or "conjugated" is defined herein as the covalent or other forms of chemical linkage of two or more molecules.

As used herein, the term "wüstite" refers to a form of iron oxides, which has an empirical formula defined as $Fe_xO$ with x in the range of about 0.83 to about 0.96.

As used herein, the term "antiferromagnetic" means magnetic material with more than one magnetic sub-lattice and substantially no net magnetic moment. Generally, antiferromagnetic materials are characterized as having a relative dielectric permeability that is less than unity, $\mu_R<1$.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate.

EXAMPLES

All syntheses were carried out using reagents that are commercially available: Iron(II) chloride, Iron(III) chloride, L-glutathione reduced, and tetrakis(hydroxymethyl)phosphonium chloride (THPC) were purchased from Sigma-Aldrich. Sodium hydroxide was obtained from Acros. Reagent solutions were prepared using Milli-Q water (Millipore Co.). All glassware used in the experiment was cleaned with freshly prepared aqua regia ($HCl:HNO_3$ volume ratio=3:1) and rinsed thoroughly in ultrapure water prior to use.

Example 1-1: Synthesis of Glutathione-Capped Magnetic Nanoparticles with THPC In a typical experiment, 0.1 mL, 10 mg/mL $FeCl_2/FeCl_3$ were added to 1 mL, 25 mg/mL glutathione solution. Subsequently, 0.01 mL THPC was added to the solution. Then 0.2 mL NaOH was added and vigorously mixed at room temperature. By reacting with glutathione for 6 hours, brown GSH—FeO NPs were generated. The crude product was then precipitated by ethanol and resuspended in water. Following this, the compounds were purified by centrifugal filtration (4000 g) for 30 min with a cutoff of 5 kDa to obtain GSH—FeO NPs. The nanoparticles were dispersed in PBS (phosphate-buffered saline) for subsequent applications.

Example 1-2: Synthesis of Insulin-Capped Magnetic Nanoparticles

All synthetic processes are the same as Example 1-1 except glutathione is replaced by insulin.

Example 1-3: Synthesis of Citrate-Capped Magnetic Nanoparticles

All synthetic processes are the same as Example 1-1 except glutathione is replaced by citrate.

To provide $T_1$ MR agents with excellent contrast (i.e. low $r_2/r_1$ ratio and magnetization) as well as biocompatibility, it is preferable to use a biocompatible capping agent, such as glutathione, during the formation of iron oxide nanoparticles. In one embodiment, using tetrakis(hydroxymethyl) phosphonium chloride (THPC) as the reducing agent, the present invention established a one-step reaction carried out in aqueous solution under atmospheric pressure and room temperature. Moreover, compared to the current ferrimagnetic NPs with magnetization (4 μB), the GSH—FeO NPs synthesized herein exhibits wüstite structure and antiferromagnetic properties, i.e., negligible magnetization and suppressed $r_2$. The high $T_1$ contrast and excellent biocompatibility make the nanoparticles of this invention superior in a variety of bio-imaging applications.

Confirmed from the results, GSH—FeO NPs were synthesized by a facile method mixing GSH solution with $FeCl_2/FeCl_3$ at pH 10. By adding THPC to the mixture as a reducing agent at room temperature under vigorous stirring for 6 hours, brown iron oxide NPs were readily prepared. After the reaction completed, the solution pH value decreased to pH~7 due to the hydroxide ion consumption. The resulting GSH—FeO NPs were purified by centrifuged filtration.

In one embodiment, the present invention also used $NaBH_4$ as a reducing agent to react with GSH and $FeCl_2/FeCl_3$. Under the characterization of XPS, the fitted peaks shift a little more to $Fe_2O_3$.

In an aim to systematically probe the pH effect on the relaxivity, the reaction was also carried out over a broad range of pH 4-11 while the iron precursor and GSH remained unchanged. The corresponding $r_1$ intensity increases from 1.9 at pH=4 to a maximum value of 4.6 at pH=7.0 and then decreases to 0.3 at pH=11. The solution pH is thus relevant to the magnetic properties of GSH—FeO NPs. The result correlates well with the reducing power of THPC, which increases as increasing the initial basicity. Evidence is also provided in TEM image of the resulting GSH—FeO NPs synthesized at pH=3, in which the particle size (~30 nm) is relatively larger than that obtained in pH=7 covering a wider range of size-distribution. In yet another approach, too much increase in reducing power causes rapid reaction and hence the adverse effect on the NPs growth, as supported by the poor GSH—FeO NPs quality synthesized in pH=11 (~6 nm).

Example 2: Nanoparticle Characterization

The size of iron oxide NPs was determined by transmission electron microscope (TEM, JEM 1230, JEOL). High resolution images of iron oxide NPs were obtained with a transmission electron microscope (TEM, JEM-2100F, JEOL) operated at 200 kV in order to determine their shape, dimension and size distribution. The specimen was prepared by drop-casting the iron oxide NPs suspension on a Cu-grid-supported quantifoil. By observing the casted materials at the hole area of the supporting film, background-less image was then obtained. Size measurements were also performed using dynamic light scattering (DLS) on a Malvem Zetasizer Nano ZS (Malvem, UK). Magnetic measurements were carried out at 300 K from −3000 to 30000 Oe using a superconducting quantum interference device (SQUID.

Quantum Design MPMS-XL7). The metal amount of samples was determined by inductively coupled plasma-mass spectrometry using an Agilent 7700e ICP/MS instrument. X-ray photoelectron spectrometry (XPS/ESCA) was used to determine the chemical state of Fe. GSH—FeO NPs were drop-casted on a Si wafer. The spectra were recorded with a PHI 5000 VersaProbe scanning ESCA microprobe (ULVAC-PHI, Japan) using a micro-focused, monochromatic Al Kα X-ray (25 W, 100 µm). The take-off angle of the photoelectron was 45°. A dual beam charge neutralizer ($Ar^+$ gun and flooding electron beam) was used to compensate for the charge up effect.

The size (diameter) of GSH—FeO NPs, measured by high-resolution transmission electron microscopy (HR-TEM), is about 3.72±0.12 nm averaged by calculating 100 particles. The lattice fringe in the single particle clearly shows $d_{hkl}$=0.251 nm, which is in good agreement with the d-spacing of planes for the wüstite FeO structure. In addition, hydrodynamic diameter distribution of GSH—FeO NPs by number in PBS was obtained from a dynamics light scattering (DLS) measurement, wherein the mean sizes of GSH and GSH—FeO NPs is 1.74±0.12 nm and 4.19±0.31 nm, respectively.

From the relaxation properties of GSH—FeO NPs measured, GSH—FeO NPs reveal a high longitudinal relaxivity (3.63 $mM^{-1}$ $s^{-1}$) and a small transverse relaxivity (8.28 $mM^{-1}$ $s^{-1}$) at 4.7 T, 40° C. The relatively low $r_2$ value ($\propto Mz$) is attributed to the intrinsic antiferromagnetic GSH—FeO NPs, which reveal very low magnetization of 0.0004 emu·$g^{-1}$ at H=3 T at 300 K. Notably, the magnetization of GSH—FeO NPs in one embodiment is four orders of magnitude smaller than any current ultrasmall iron oxide NPs (>5 emu·$g^{-1}$), ensuring the low $r_2$ and hence the $r_2/r_1$ ratio.

Example 3: In-Vitro Cytotoxicity

The toxicity of the iron oxide NPs is examined by using a colorimetric assay. The HeLa cell line, derived from the human cervical cancer cell, is chosen for cytotoxicity evaluation. The cells are cultured in 90% minimum essential medium (MEM; Cellgro Herndon, Va., USA) supplemented with 10% heat-inactivated fetal bovine serum, penicillin (50 U/mL), and streptomycin (0.05 mg/mL). For cell expansion and senescence induction, the cells are cultured at 37° C. in a humidified atmosphere of 5% $CO_2$/95% air and passaged by trypsinization. To examine the cytotoxicity, various concentrations of nanocomposites, 0, 25, 50, 100, 150, and 200 µg/mL were added to each HeLa cell sample and incubated for 24 hours. As for the iron oxide NPs, the result of the MTT (3-(4,5-dimethylthiazol-2-yl)-2,5-diphenyltetrazolium bromide) test reveals that almost 100% of the cells are viable even after incubation with a dose of as high as 0.25 mM. After 24 hours of incubation, the viability of HeLa cells is still above 90% at all Fe incubation concentrations.

Example 4: Cellular Labeling

For microscopic observation, HeLa cells were seeded in 6-well plate with 5×$10^4$ cell/well density in 2 mL serum-free culture medium to promote the uptake of nanoparticles. After 4 hours incubation time with 0.25 mM iron oxide NPs, cells were washed three times with PBS and then fixed with 4% paraformaldehyde in PBS. The cells were washed twice with PBS and then were stained with 1 ml Prussian blue solution mixed with equal volume of 2N hydrochloric acid and 2% potassium ferrocyanide solution. The cell samples were observed by OLYMPUS Inverted Microscope Model: IX81 equipped with UPLSAPO60XO objective, and using halogen lamp as light source.

Example 5

In-Vitro MR Imaging

MRI was performed using a clinical 3 T MR system (Signa Infinity Twinspeed, GE Healthcare, USA). The cell samples were centrifuged in test tubes bathing in a home-made water tank. The tank was then placed in an 8 channel head coil. Two dimension $T_2$-weighted fast spin echo pulse sequences were used (TR/TE=550/13 ms). The slice thickness was 1.5 mm with a 0.2 mm gap and the field of view (FOV) was 14×7 cm. The matrix size is 288×192. Total scan time was 2 min and 46 s at the NEX of 3. The images were then analyzed at the workstation provided by GE Healthcare (Advantage workstation 4.2).

For Examples 4 and 5, the result from Prussian blue staining demonstrates a noticeable imaging capability and cell internalization ability of GSH—FeO NPs that are incubated with HeLa cells. In addition, the GSH—FeO NPs encapsulated in HeLa cells show apparent signal intensity enhancement as iron content increases under $T_1$ weighted images, indicating that GSH—FeO NPs induced contrast enhancement in a dose-dependent manner with excellent biocompatibility for cellular MR imaging.

$T_1$ and $T_2$-weighted MR image of GSH—FeO NPs solutions at gradient Fe concentration is confirmed with inductively coupled plasma mass spectrometry (ICP-MS). Under $T_1$-weighted images, noticeable increase of signal intensity was found as the GSH—FeO concentration increased, whereas the drop of signal intensity was observed under $T_2$ weighted image.

Example 6: In Vivo Experiment

All the animals were initially anesthetized with 5% isoflurane at the flow rate of 1 L $min^{-1}$. After induction of the anesthesia, Isoflurane was then maintained at the concentration of 1-1.5% and 0.8-1.2% for rat and mouse, respectively, at the flow rate of 1 L $min^{-1}$ throughout the experiments. For evaluating the vasculature of the brain, Balb/C mice were placed in a prone position and were fitted with a custom-designed head holder inside the magnet of a Pharmascan 7 T spectrometer before and after iron oxide NPs injection at the time interval of 10, 30, 60, 120 and 1,440 minutes. The parameters of the scanning are TR=500 ms, TE=12 ms, Field of view (FOV)=2×2 cm at the slice thickness of 1 mm with the matrix size of 256×128 (zero-padded to 256×256) with ten repetitions. For in vivo intravenous administration, the nanoparticles were suspended in PBS buffer (0.1 mL) and were administered from tail vein at a dose of 5 mg Fe $kg^{-1}$ (body weight).

For further studying the renal imaging, Sprague-Dawley rat body experiments were performed in a Biospec 4.7 T spectrometer before and after the injection of iron oxide NPs at the interval of 10, 30, 60, 120 and 1.440 minutes. The scanning parameters were TR($T_1/T_2$)=500/5000 ms, TEeff ($T_1/T_2$)=8/70 ms, FOV=7×7 cm, slice thickness=1.3 mm, and matrix size=256×128 (zero-padded to 256×256) with six repetitions. Typically, nanoparticles suspended in PBS buffer (0.1 mL) were administered to Sprague-Dawley rat (8 weeks of age, body mass is ≈300 g) via femoral vein injection at a dose of 5 mg Fe $kg^{-1}$ (body weight). The percentage of signal-to-noise (SNR) change for pre-injection versus post-injection $T_2WI$ and $T_2WI$ were calculated according to the following formula: % SNR difference=100×((SNR)$_{post}$−(SNR)$_{pre}$)/(SNR)$_{pre}$.

FIG. 1 shows strong enhancement in mice's superior sagittal sinus, an important venous structure of the brain that drains most of the blood into heart. The signal to noise ratio (SNR) of sagittal sinus before and after administration is up to 318.6%, but the SNR in cortex remains nearly unchanged (1.2%). Also, the bilateral internal carotid arteries are well enhanced, showing their efficacy for detecting cerebral arterial occlusion. The long circulation time in the vasculature, compared with traditional gadolinium-based $T_1$ contrast agents, makes GSH—FeO NPs potent vascular diagnosis agent for disease diagnosis such as arterial occlusion that commonly seen in stroke patients and venous thrombosis that exists in coagulation abnormal populations.

Figure 2:
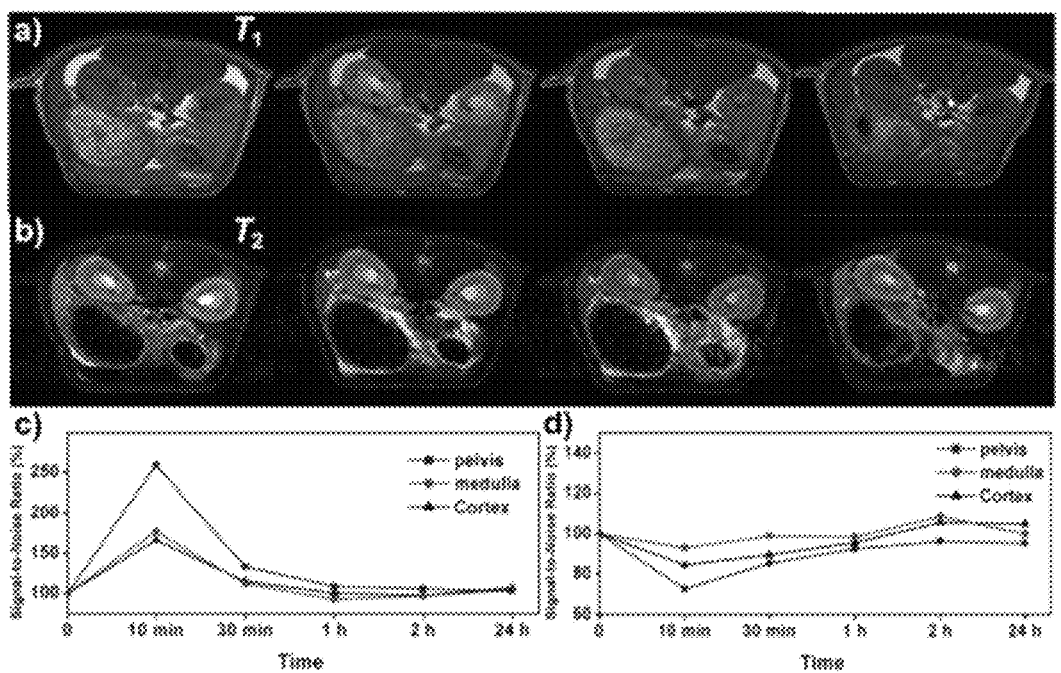
FIG. 2 shows: a) $T_1$ and b) $T_2$ weighted in vivo MR images at 0, 10 min. 30 min, and 24 h from left to right, and c) $T_1$ and d) $T_2$ signal intensity of kidney along the time interval obtained using GSH—FeO NPs.

FIGS. 2a and 2b show $T_1$ and $T_2$ weighted MRI images of rat's kidney after GSH—FeO NPs administration. The renal cortex is clearly visualized 10 minutes after administering GSH—FeO NPs, indicating a rapid glomerular filtration process. High signal intensity changes in renal pelvis were also noticed, which reflects efficient particle excretion into urine. Accordingly, a quantitative measurement on the changes of SNR difference is shown in FIGS. 2c and 2d. In comparison to the pre-contrast images, under $T_1$, weighted images, the signal intensity of renal cortex increased by 168% after 10 minutes of injection, and then fully recovered at the end of experiment. Evidently, the GSH—FeO NPs are well secreted by kidneys and hence serve as an ideal contrast agent for investigating renal anatomy, glomerular physiology and neoplastic disease process. As for the liver, there was no apparent $T_1$ signal enhancement and $T_2$ change. Compared to the strong T1 enhancement in renal pelvis after mouse tail injection, only a weak T1 contrast in liver (~20%) could be observed, this result implies that most GSH—FeO NPs could escape the reticuloendothelial system (RES) of liver and then excreted in the body via kidney system. Because most of the known NPs that waived RES surveillance had the surface modification of polyethylene glycol (PEG), the GSH—FeO NPs of this invention might open a new gate for biomolecule targeting study, in which bypassing the RES achieves higher targeting efficiency toward interested molecule and cells.

The above detailed description is merely illustrative in nature and is not intended to limit the embodiments of the subject matter or the application and uses of such embodiments. As used herein, the term "exemplary" means "serving as an example, instance, or illustration." Any implementation described herein as exemplary is not necessarily to be construed as preferred or advantageous over other implementations.

Moreover, while at least one exemplary embodiment has been presented in the foregoing detailed description, it should be appreciated that a vast number of variations exist. It should also be appreciated that the exemplary one or more embodiments described herein are not intended to limit the scope, applicability, or configuration of the claimed subject matter in any way. Rather, the foregoing detailed description will provide those skilled in the art with a convenient guide for implementing the described one or more embodiments. Also, various changes can be made in the function and arrangement of elements without departing from the scope defined by the claims, which include known equivalents and foreseeable equivalents at the time of filing this patent application.

What is claimed is:

1. A magnetic nanoparticle composition, comprising an iron oxide particle core conjugated with a capping agent and having wüstite structure and antiferromagnetic properties, wherein the empirical formula of iron oxide is defined as $Fe_xO$ with x in the range of about 0.83 to about 0.96, and wherein the iron oxide particle core exhibits an $r_2/r_1$ ratio of about 1 to about 10, where $r_2$ represents transverse relaxivity and $r_1$ represents longitudinal relaxivity.

2. The composition according to claim 1, which is in an aqueous phase and has a pH of about 4 to about 12.

3. The composition according to claim 1, wherein the iron oxide particle core has a particle size of less than 50 nm.

4. The composition according to claim 3, wherein the iron oxide particle core has a particle size of less than 20 nm.

5. The composition according tea claim 1, wherein the capping agent is a biocompatible capping agent selected from a group consisting of glutathione, glutamic acid, dextrin, starch, glucose, chitosan, citrate, citric acid, ascorbic acid, insulin, bovine serum albumin, keratin, arginine, curcumin and protamine.

6. The composition according to claim 5, wherein the biocompatible capping agent is glutathione.

7. The composition according to claim 5, wherein the capping agent is conjugated with a targeting agent or a therapeutic agent.

8. A method of manufacturing the composition according to claim 1, comprising:
   preparing a mixture containing ferrous salt, ferric salt and the capping agent; and
   adding a reducing agent to the mixture to initiate a redox reaction at room temperature, thereby forming the iron oxide particle core conjugated with the capping agent;
   wherein the composition is in an aqueous phase.

9. The method according to claim 8, wherein the molar ratio of [$Fe^{2+}$] to [$Fe^{3+}$] is about 0.2 to about 5.

10. The method according to claim 9, wherein the molar ratio of [$Fe^{2+}$] to [$Fe^{3+}$] is about 0.5 to about 2.

11. The method according to claim 8, wherein the reducing agent is selected from a group consisting of tetrakis (hydroxymethyl)phosphonium chloride, borohydride, hydrazine, caustic alkali, hydroxyl amine, ammonium hydroxide, citrate, citric acid, ascorbic acid and a mixture thereof.

12. The method according to claim 11, wherein the reducing agent is tetrakis(hydroxymethyl) phosphonium chloride.

13. The method according to claim 8, wherein the ferrous salt is selected from a group consisting of ferrous chloride, ferrous chloride tetrahydrate, ferrous acetate, ferrous lactate, ferrous: oxalate and a mixture thereof; and the ferric salt is selected from a group consisting of ferric chloride, ferric chloride hexahydrate, ferric acetate, ferric acetylacetonate, ferric oxalate, ferric nitrate, ferric nitrate nonahydrate and a mixture thereof.

14. The method according to claim 8, wherein the capping agent is a biocompatible capping agent selected from a group consisting of glutathione, glutamic acid, dextrin, starch, glucose, chitosan, citrate, citric acid, ascorbic acid, fatty acid, insulin, bovine serum albumin, keratin, arginine, curcumin and protamine.

15. The method according to claim 14, wherein the biocompatible capping agent is glutathione.

16. A contrast agent for magnetic resonance imaging comprising the composition according to claim 1.

17. The contrast agent of claim 16, which is a $T_1$ contrast agent.

18. A method of acquiring an image, comprising:
administering the contrast agent according to claim 16 to a recipient; and
acquiring a magnetic resonance image of the recipient.

19. A method for delivering a therapeutic or diagnostic agent, comprising administering the composition according to claim 1 to a recipient, wherein the therapeutic or diagnostic agent is conjugated with the iron oxide particle core or the capping agent.

* * * * *